United States Patent
Viswanath et al.

(10) Patent No.: US 9,287,862 B2
(45) Date of Patent: Mar. 15, 2016

(54) BOOTSTRAPPED SAMPLING SWITCH CIRCUITS AND SYSTEMS

(71) Applicant: Texas Instruments Incorporated, Dallas, TX (US)

(72) Inventors: Rakul Viswanath, Tamil Nadu (IN); Rahul Sharma, Karnataka (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 14/533,787

(22) Filed: Nov. 5, 2014

(65) Prior Publication Data

US 2015/0188533 A1    Jul. 2, 2015

Related U.S. Application Data

(60) Provisional application No. 61/920,817, filed on Dec. 26, 2013.

(51) Int. Cl.
| | |
|---|---|
| *H02M 3/07* | (2006.01) |
| *H03K 17/06* | (2006.01) |
| *H03K 17/16* | (2006.01) |
| *H03M 3/00* | (2006.01) |
| *H05G 1/70* | (2006.01) |
| *G01N 23/04* | (2006.01) |

(52) U.S. Cl.
CPC ............ *H03K 17/063* (2013.01); *G01N 23/046* (2013.01); *H03K 17/16* (2013.01); *H03M 3/496* (2013.01); *H05G 1/70* (2013.01); *H03K 2217/0036* (2013.01)

(58) Field of Classification Search
CPC .... B60Q 11/005; H01H 13/023; B61L 7/061; F02P 17/00; F21S 8/08
USPC ...................... 327/91–97, 536, 589
See application file for complete search history.

(56) References Cited

U.S. PATENT DOCUMENTS

| | | | |
|---|---|---|---|
| 8,766,835 B2 | 7/2014 | Hojabri et al. | |
| 8,890,577 B1 * | 11/2014 | Trampitsch | ..................... 327/94 |
| 2004/0041613 A1 * | 3/2004 | Chen | .............................. 327/333 |
| 2012/0313670 A1 * | 12/2012 | Thomas | ........................ 327/109 |

OTHER PUBLICATIONS

Texas Instruments, Inc., "AFE1256 256-Channel, Analog Front-End for Digital X-Ray, Flat-Panel Detectors," www.ti.com, SBAS630B, Oct. 2013, Revised Apr. 2014, pp. 1-8, product data sheet, retrieved from world wide web, uniform resource locator: http://www.ti.com/lit/ds/symlink/afe1256.pdf, on Nov. 5, 2014.
Texas Instruments, Inc., "CT Scanner," www.ti.com, Applications, retrieved from world wide web, uniform resource locator: http://www.ti.com/solution/ct_scanner, on Sep. 28, 2014.
G. Pandey, A. Sahu, G. Sinha, "Resetting 2-Order Sigma-Delta Modulator in130 nm CMOS Technology," International Journal of Advanced Research in Computer Engineering & Technology, vol. 3 Issue 7, Jul. 2014, pp. 2429-2434, India.

* cited by examiner

*Primary Examiner* — Quan Tra
(74) *Attorney, Agent, or Firm* — Gregory J. Albin; Frank D. Cimino

(57) ABSTRACT

A bootstrap circuit for a sampling transistor. A circuit includes a MOS transistor having a source terminal coupled to an input for receiving an input voltage; an output at a drain terminal of the MOS transistor coupled to one plate of a sampling capacitor; a first switch coupling the input voltage to a gate terminal of the MOS transistor responsive to an initial phase control signal; a bootstrap capacitor having a top plate coupled to the gate terminal of the MOS transistor and coupled to the first switch; a second switch coupling a bottom plate of the bootstrap capacitor to a first low voltage supply responsive to the initial phase control signal; a third switch coupling the bottom plate of the bootstrap capacitor to a positive voltage supply greater than the first low voltage supply responsive to a first phase periodic control signal. Additional circuits and systems are disclosed.

20 Claims, 4 Drawing Sheets

BOOTSTRAPPED SAMPLING SWITCH CIRCUITS AND SYSTEMS

RELATED APPLICATIONS

This patent application claims priority to U.S. Provisional Application Ser. No. 61/920,817, entitled "A Bootstrapped Sampling Switch for a Reset Delta Sigma ADC," filed Dec. 26, 2013, which is hereby incorporated by reference herein in its entirety.

TECHNICAL FIELD

Aspects of the present application relate generally to the use of bootstrap circuits for analog to digital converters and in particular to resettable delta-sigma analog to digital converters. Applications of resettable delta-sigma analog to digital converters include, as a non-limiting example, performing analog to digital conversion for use in imaging systems such as X-ray systems for medical imaging and for security applications, and X-ray computed tomography (CT) scanners.

BACKGROUND

High performance analog to digital converters (ADCs) are increasingly required for precise digital processing of analog signals. Applications include receiving low-level current signal outputs from photo-detectors such as in imaging systems. Such imaging systems can include, for example, X-ray imaging systems. In a further application, the X-ray technology is combined with photo-detectors in a ring configuration to form computed tomography (CT) scanners used in medical diagnostics, for example.

Recent improvements for analog to digital converters (ADCs) include the use of resettable delta-sigma ADCs. In such an ADC, the memory elements are all reset before each new conversion. The input signal is assumed to be stable during each conversion cycle. This input signal is repeatedly sampled, each sample is compared to a reference voltage level to determine a corresponding data bit, the data bits are quantized by a clocking sampling circuit to create a plurality of conversion samples, and the conversion samples are averaged. The repeated sampling is done to reduce or eliminate the effects of noise such as quantization noise and thermal noise on the digital representation of the analog signal. As the analog input does not change during a conversion cycle, the input voltage can be sampled on a capacitor and placed in feedback around a driver amplifier. The output of the driver amplifier can then drive the switched sampling capacitor of the first stage of an ADC.

FIG. 1A depicts in a simple block diagram an input stage 10 for an ADC of the prior art. In FIG. 1A, an input "Vin" is sampled onto the capacitor C1. The output of the driver circuit is a voltage "Vin" which is the input for the remainder of the circuit 10.

As is known to those skilled in the art, the input stage to an ADC can be implemented as a switched capacitor sampling stage. Here the sampling capacitor labeled Csamp is coupled to the Vin voltage output of the driver circuit 13 and capacitor C1 by a two phase switching circuit. The operation of the switching circuitry is now described. Assume all switches 11, 15, 17 and 21 in FIG. 1A are initially open. Switch 11 and switch 17 are closed in a sampling operation responsive to a first periodic control signal PHI_1, and when these switches are closed, capacitor Csamp receives the voltage Vin (minus a supply voltage Vss (or ground)). In order to subsequently transfer the stored voltage from capacitor Csamp into the rest of the converter circuitry ADC 19, the switch 11 and switch 17 are opened, and switches 15 and 21 subsequently closed. These switches 15 and 21 are controlled by a second periodic control signal PHI_2, and when PHI_2 is active, the voltage on capacitor Csamp is transferred to the ADC 19. ADC 19 can include a comparator and a quantizer for clocking samples of the voltage stored on Csamp and for outputting a plurality of digital bits that represent a voltage level for the analog input. An average of the oversampled data can be taken in a decimator to get an accurate digitized signal corresponding to the analog input signal.

The control signals PHI_1 and PHI_2 are periodic non-overlapping control signals that repeatedly sample the output voltage of the integrator circuit, labeled voltage Vin in FIG. 1A, into the ADC 19 during an analog conversion cycle. FIG. 1B illustrates in a simple timing diagram the timing of periodic control signals PHI_1 and PHI_2. In operation, the signals repeatedly cause the switches to close and thus control the sampling of voltage Vin into capacitor Csamp, and the transfer from Csamp into the ADC 19. Importantly, the signals PHI_1 and PHI_2 must not overlap, e.g., must not be active at the same point in time. In the illustrative example shown in FIG. 1B, the signals have a 50% duty cycle, but other duty cycles can be used. Typically the duty cycles for PHI_1 and PHI_2 can be similar or equal, but alternatives with asymmetric or non-equal duty cycles can also be used.

In the switched capacitor sampling stage 10, a prior known solution operates the sampling switch 11 using a bootstrap circuit. Using a bootstrap circuit with a bootstrap capacitor places a higher voltage at the gate during a turn on operation for an N-type MOS transistor that is used as the sampling switch 11, and so ensures rapid turn-on of the transistor. FIG. 2 depicts, for example, a prior art solution using a transistor M1 configured as the sampling switch 11 in FIG. 1, operated with a bootstrap capacitor Cb. During the first phase, when the control signal PHI_2 is active, switches 31 and 33 are closed and capacitor Cb is charged to VDD−VEE, where VDD is a positive supply voltage, and VEE is the most negative supply voltage in the system, which can be zero volts for example. At the same time switch 41 is closed and ensures that N-type MOSFET M1 is turned off by placing VEE at the gate terminal.

In the second phase of the operation of the circuit of FIG. 2, control signal PHL_1 is high and switches 35, 39 are closed while switches 31, 33 and 41 are opened. The voltage stored on bootstrap capacitor Cb, which is voltage VDD when VEE is zero volts, is now added to the input voltage Vin so that the voltage on the gate terminal of transistor M1 is now boosted to the input voltage Vin+VDD, turning on the transistor M1. Vin is also at the source terminal of transistor 43. The transistor M1 is turned on and so acts as the "closed" switch 11 in FIG. 1A, and the output voltage Vout receives the voltage Vin while the transistor M1 is turned on.

In order to provide high performance in the ADC circuit that incorporates the bootstrap circuit and the sampling switch, the circuit must have a more or less constant resistance, so as to provide highly linear results. Importantly the resistance should be independent of the voltage Vin, as this integrator circuit output voltage varies with the analog voltage being converted. The on resistance Rdson for the transistor M1 is proportional to the gate to source voltage (Vgs) for the transistor. While transistor M1 in FIG. 2 is turned on, the gate voltage is at (Vin+VDD). The source voltage is at Vin, so the voltage Vgs for transistor M1 is (Vin+VDD)−Vin, or simply VDD. This is an important feature of the prior known solution for switched capacitor bootstrap circuit 30 shown in FIG. 2. Because the gate to source voltage Vgs of transistor M1 is independent of the input voltage Vin, which varies with the analog input voltage, the circuit operates to provide a more linear performance for the ADC by presenting a constant on-resistance over many cycles.

In operation of the ADC circuit including the bootstrap circuit of FIG. 2, the input voltage is sampled onto the capacitor C1 of the driver circuit 13 once per conversion cycle, for example in a resettable sigma delta ADC, and then the switched capacitor circuit including the sampling capacitor Csamp samples that Vin voltage value many times. When the prior known solution bootstrap circuit 30 shown in FIG. 2 is used, the driver 13 has to drive the capacitor Cb each time the control signal PHI_1 is active. The driver 13 is also coupled to drive the bottom plate of the bootstrap capacitor Cb, which has a large parasitic capacitance. Since the periodic sampling occurs many times for each analog conversion cycle, this is a substantial load on the driver amplifier 13 and consumes power for each of the sampling cycles of the ADC operations. Further the driver 13 has to charge the gate capacitance of the transistor M1 for each cycle, and because the input voltage Vin is coupled to the gate terminal, some non-linear effects still occur. The need to drive the bottom plate of the bootstrap capacitor and the gate of the MOS transistor, and the corresponding parasitic capacitances, each time PHI_1 is active, causes increased power dissipation. Further, the gate capacitance and the bottom plate of the bootstrap capacitor Cb are charged to a voltage such as VEE and VDD respectively, in the off phase, and in the on phase (PHI_1 is active), these parasitic capacitances cause large load steps on the driver.

Improvements in the bootstrap circuitry for switched capacitor sampling circuits, such as for the input stage of ADCs, are therefore needed to address the deficiencies and the disadvantages of the prior known approaches. Solutions are needed that reduce power, and which improve the performance of the circuits.

SUMMARY

Various aspects of the present application provide improved novel bootstrap circuits for a sampling transistor, such as in a switched capacitor circuit. In an application, the sampling transistor couples an input voltage to a sampling capacitor in an input stage for an analog to digital converter. The novel circuits of the present application reduce the power consumption of the bootstrap circuit while providing a highly linear circuit with excellent performance in an ADC application.

In one aspect of the present application, a bootstrap circuit for a sampling transistor for a switched capacitor is provided, including: a MOS transistor having a source terminal coupled to an input for receiving an input voltage; an output at a drain terminal of the MOS transistor coupled to one plate of a sampling capacitor; a first switch coupling the input voltage to a gate terminal of the MOS transistor responsive to an initial phase control signal; a bootstrap capacitor having a top plate coupled to the gate terminal of the MOS transistor and coupled to the first switch; a second switch coupling a bottom plate of the bootstrap capacitor to a first low voltage supply responsive to the initial phase control signal; a third switch coupling the bottom plate of the bootstrap capacitor to a positive voltage supply greater than the first low voltage supply responsive to a first phase periodic control signal; and a fourth switch coupling the bottom plate of the bootstrap capacitor to a second low voltage supply lower than the first low voltage supply, responsive to a second phase periodic control signal.

In a further aspect of the present application, in the above described circuit, wherein the first switch and the second switch are closed during an initial phase responsive to the initial phase control signal, coupling the top plate of the bootstrap capacitor to the input voltage and charging the bootstrap capacitor to the input voltage.

In a further aspect of the present application, in the above described circuit, wherein the third switch is closed during each high portion of the first phase periodic control signal, boosting the gate voltage of the MOS transistor to a voltage that is a sum of the input voltage stored on the bootstrap capacitor and the positive supply voltage.

In still another aspect of the present application, in the bootstrap circuit described above, wherein the fourth switch is closed during each high portion of the second phase periodic control signal, coupling the gate of the MOS transistor to the second low voltage plus the input voltage stored on the bootstrap capacitor.

In still a further aspect of the present application, in the above described bootstrap circuit, wherein the input voltage is coupled to the sampling capacitor during each high portion of the first phase periodic control signal by a current conduction path of the MOS transistor, which is turned on by the boosted gate voltage.

In still another aspect of the present application, in the above described bootstrap circuit, wherein the MOS transistor is an N-type MOS transistor.

In a further aspect of the present application, in the above described bootstrap circuit, wherein each of the first, second, third and fourth switches comprise a MOS transistor.

In yet another aspect of the present application, in the above described bootstrap circuit, wherein the first, second, third and fourth switches each comprise an N-type MOS transistor.

In yet another aspect of the present application, in the bootstrap circuit described above, wherein the initial phase control signal is high only for an initial portion of a sampling cycle, and the first phase periodic control signal and the second phase periodic control signal are repeating periodic signals that continue for a remaining portion of the sampling cycle, the first and the second periodic control signals having similar duty cycles that are non-overlapping.

In an alternative arrangement that incorporates features of the present application, an analog to digital converter integrated circuit is provided, including a plurality of inputs each configured to receive an analog input signal; a plurality of resettable delta sigma analog to digital converter stages, each comprising: a plurality of driver circuits, each coupled to a respective one of the plurality of inputs, each comprising an amplifier and an integrator capacitor and outputting a sampled input voltage; a plurality of switched capacitor input stages, each coupled to receive at least one of the sampled input voltages at an input, each of the switched capacitor input stages further comprising: the input receiving the sampled input voltages and coupled to a source terminal of a MOS transistor; an output at a drain terminal of the MOS transistor coupled to one plate of a sampling capacitor; a first switch coupling the input to a gate terminal of the MOS transistor, responsive to an initial phase control signal; a bootstrap capacitor having a top plate coupled to a gate terminal of the MOS transistor and to the first switch; a second switch coupling a bottom plate of the bootstrap capacitor to a first low voltage supply responsive to the initial phase control signal; a third switch coupling the bottom plate of the bootstrap capacitor to a positive voltage supply greater than the first low voltage supply responsive to a first phase periodic control signal; and a fourth switch coupling the bottom plate of the bootstrap capacitor to a second low voltage supply lower than the first low voltage supply, responsive to a second phase periodic control signal.

In still another aspect of the present application, the analog to digital converter circuit is provided, and further includes: control circuitry coupled to provide the initial phase control signal at an initial portion of a sampling operation, and further coupled in a run portion of the sampling operation to subsequently provide the first phase periodic control signal and the second phase periodic control signal as repeating periodic signals that are non-overlapping.

In yet another aspect of the present application, the analog to digital converter circuit described above is provided, and further includes a plurality of analog to digital converter stages coupled to respective ones of the sampling capacitors and configured to output digital data corresponding to the analog input signals.

In yet another aspect of the present application, the analog to digital converter circuit described above is provided wherein the MOS transistors are N-type MOS transistors.

In still a further aspect of the present application, the analog to digital converter circuit described above is provided, wherein during a high portion of the first phase periodic control signal, the voltage input at the source of the MOS transistors is coupled to the drain of the MOS transistors and to the sampling capacitor, due to the gate to source voltage of the MOS transistors which is boosted by the bootstrap capacitor to the positive supply voltage.

In another aspect of the present application, a system for imaging is provided, including an apparatus for creating images comprising a plurality of radiation emitters spaced from and directed towards a plurality of photo-detectors sensitive to the emitted radiation, the plurality of photo-detectors outputting analog output signals corresponding to an intensity of the radiation received at the photo-detectors; at least one analog-to-digital converter integrated circuit having a plurality of inputs coupled to receive analog output signals from the plurality of photo-detectors, and further including: a plurality of analog to digital converter stages including an analog-to-digital converter stage configured to output digital data corresponding to the analog output signals, each of the analog to digital converter stages comprising: a plurality of driver circuits, each coupled to a respective one of the plurality of inputs, each comprising an amplifier and a capacitor coupled to sample an analog signal and each outputting a corresponding input voltage; a plurality of switched capacitor input stages, each coupled to the output of at least one of the driver circuits, each of the switched capacitor input stages further comprising: a MOS sampling transistor having a current conduction path coupled between the input voltage and an output, and having a gate terminal; one plate of a sampling capacitor coupled to the output of the MOS sampling transistor; a first switch coupling the input voltage to the gate terminal of the MOS sampling transistor, responsive to an initial phase control signal; a bootstrap capacitor having a top plate coupled to the gate terminal of the MOS sampling transistor and to the first switch; a second switch coupling a bottom plate of the bootstrap capacitor to a first low voltage supply responsive to the initial phase control signal; a third switch coupling the bottom plate of the bootstrap capacitor to a positive voltage supply greater than the first low voltage supply, responsive to a first phase periodic control signal; and a fourth switch coupling the bottom plate of the bootstrap capacitor to a second low voltage supply lower than the first low voltage supply, responsive to a second phase periodic control signal.

In still another aspect of the present application, the system for imaging described above is provided, wherein the MOS sampling transistors in each of the switched capacitor input stages further comprise an N-type MOS transistor. In yet another aspect of the present application, the system for imaging described above is provided, wherein the first, second, third and fourth switches of each of the switched capacitor input stages further comprise MOS transistors.

In still another aspect of the present application, the system for imaging described above is provided and further includes: a control circuit within the analog to digital converter integrated circuit, the control circuit outputting the initial phase control signal at an initial portion of an analog signal conversion cycle, and subsequently outputting for a remaining portion of an analog signal conversion cycle the first periodic control signal and the second periodic control signal as repeating periodic signals are non-overlapping.

In yet another aspect of the present application, the system for imaging described above is provided, wherein the system is a computed tomography X-ray scanning system. In an alternative aspect of the present application, the system for imaging described above is provided, wherein the system is an X-ray baggage scanning system.

Recognition is made in aspects of this application of a solution for novel bootstrap circuits for sampling switches that provide improved power consumption and highly linear performance. The novel bootstrap circuits surprisingly overcome the problems and deficiencies of the known prior circuits, without degrading the performance characteristics of the circuits.

BRIEF DESCRIPTION OF THE DRAWINGS

For a more complete understanding of the illustrative embodiments described herein and the advantages thereof, reference is now made to the following descriptions taken in conjunction with the accompanying drawings, in which.

Corresponding numerals and symbols in the different figures generally refer to corresponding parts unless otherwise indicated. The figures are drawn to clearly illustrate the relevant aspects of various aspects of the application and are not necessarily drawn to scale.

DETAILED DESCRIPTION

Figure 1A:
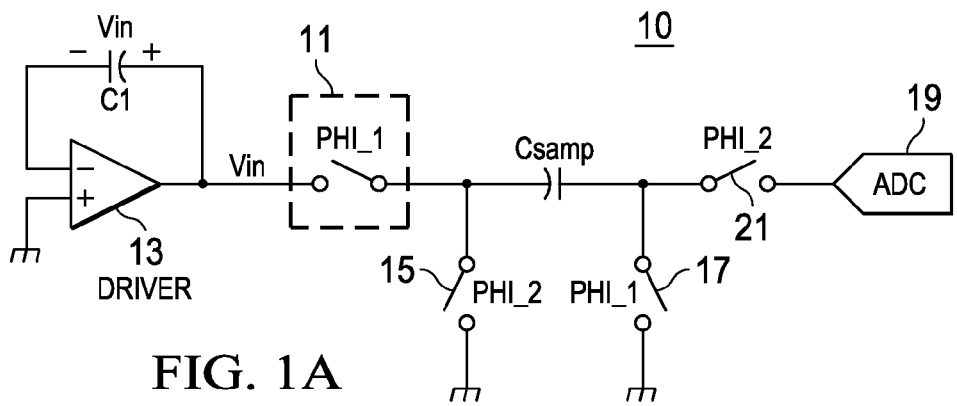
FIG. 1A and FIG. 1B illustrate in a simplified circuit diagram, a portion of a prior art ADC circuit and the timing for associated control signals.
Figure 1B:
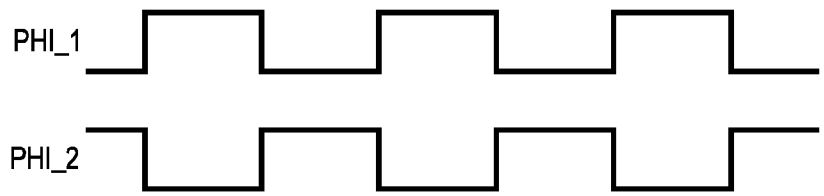

The making and using of example illustrative arrangements that incorporate various features of the present application are discussed in detail below. It should be appreciated, however, that the example arrangements presented provide many applicable inventive concepts that can be embodied in a wide variety of specific contexts. The specific example arrangements and alternative arrangements that are discussed are merely illustrative of specific ways to make and use the various features of the present application discovered by the inventors, and the examples described do not limit the scope of the specification, nor do the examples described limit in any way the scope of the appended claims.

For example, when the term "coupled" is used herein to describe the relationships between elements, the term as used in the specification and the appended claims is to be interpreted broadly, and is not to be limited to "connected" or "directly connected" but instead the term "coupled" may include connections made with intervening elements, and additional elements and various connections may be used between any elements that are "coupled."

In the arrangements that incorporate features of the present application, novel solutions are provided for reducing the power consumed in driving the input sampling stage of a switched capacitor circuit. In an example illustrative application, the input sampling stage is an input stage for a delta sigma ADC circuit. Such circuits are used, for example, when relatively low level analog signals are sensed and converted to digital signals for further processing. In an example application, current from an array of photo-detector devices is output to an integrated circuit that has a plurality of ADC converters in channels for each of the current outputs of the photo-detector. The integrated circuit may be, for example, an analog front end (AFE) or a dual direct current (DDC) device from Texas Instruments, Incorporated. Non-limiting examples of such integrated circuits include commercially available Texas Instruments parts such as the AFE1256 256 channel analog front end integrated circuit, and the DDC1128 128 Channel Current Input ADC integrated circuit. The features and arrangements of the present application including the discoveries made by the inventors may be incorporated into such integrated circuits to improve performance.

In some applications the photo-detectors may be an array of photo-detectors used with an X-ray device such as a medical or dental X-ray device, a security screening X-ray device or a computed tomography X-ray scanner, or CT scanner. The features of the present application provide solutions that overcome the problems of the known prior approaches for these applications.

In a first illustrative arrangement, it is recognized by the inventors of the present application that in the input sampling stage to each ADC stage, which is a switched capacitor circuit that couples an output signal from a driver amplifier to a sampling capacitor, it is not necessary for the driver circuit to charge a bootstrap capacitor many times over a single analog to digital conversion cycle. In an example application for a resettable sigma delta ADC converter, the input signal is sampled once and then converted many times and the results are averaged, and then the ADC converter is reset. The use of many samples of the stored input voltage eliminates variations in the output due to random and quantization noise and the like. However, the input voltage Vin does not change during these many samples in the conversion cycle.

In an illustrative arrangement of the present application, it is advantageously recognized by the inventors of the application that it is surprisingly possible to charge a bootstrap capacitor with the input signal just once per conversion cycle, and then, to relieve the driver amplifier from further charging the bootstrap capacitor for the remaining portion of the conversion cycle, until the ADC converter is reset again and a new analog to digital conversion cycle begins.

Figure 3:
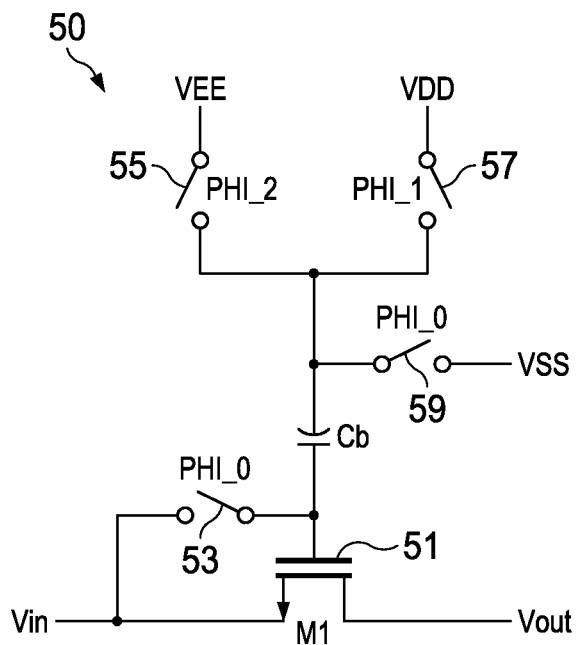
FIG. 3 illustrates in a simplified circuit diagram an example embodiment bootstrap circuit for a sampling switch.

FIG. 3 depicts in a simple circuit diagram a portion of an input circuit 50 of an ADC converter including the sampling switch. In FIG. 3, the sampling switch is implemented as an N-type MOSFET device M1, although other devices could be used for the sampling switch, including P-type MOSFETs, depletion mode MOSFETs, transmission gates including a P-type and N-type MOSFETs coupled in parallel, and the like. Those skilled in the art will recognize that the illustrative arrangements of the present application presented herein can be modified to use other sampling switch types to achieve the advantages described herein with respect to the illustrative non-limiting example of FIG. 3, and the alternative circuits obtained using these modifications are contemplated as additional alternative arrangements incorporating features of the present application and which fall within the scope of the appended claims.

FIG. 3 illustrates an example illustrative arrangement of the present application including a novel bootstrap circuit for turning on the switch formed by transistor M1. A boost capacitor Cb is coupled to the gate terminal of sampling switch M1. The timing signals and the switches to charge the bootstrap capacitor Cb are now modified to use a three phase approach that is in sharp contrast to the prior known solutions. In an initial phase, control signal PHI_0 is coupled to the switch 53 and also to switch 59. The switch 53 couples the top plate of the capacitor Cb to the input voltage Vin.

Importantly the input voltage Vin in FIG. 3 is the output of a driver circuit such as shown in FIG. 1A, and the input voltage Vin doesn't change during the analog signal conversion cycle, which is the time period of interest. PHI_0 is also controlling the switch 59, which couples the bottom plate of the capacitor to a low voltage VSS. Voltage VSS is a low voltage but not necessarily the lowest voltage available in the circuit, and voltage VSS may be adjusted depending on the analog voltage range for Vin, and other characteristics such as the level of the positive supply voltage VDD. Switch 55 is controlled by PHI_2, a periodic control signal. This switch couples the bottom plate of the capacitor Cb to the lowest voltage in the system, VEE. Switch 57 is controlled by PHI_1, a periodic control signal which couples the bottom plate of the capacitor Cb to the positive supply voltage VDD. Also importantly the driver circuit (not shown in FIG. 3) now drives the top plate of the bootstrap capacitor Cb. The top plate of capacitor Cb in FIG. 3 has a lower parasitic capacitance than the bottom plate of the capacitor which the prior art driver circuit repeatedly has to drive in the prior known solutions, thus the power dissipated is reduced by use of the features of the present application.

Figure 4:
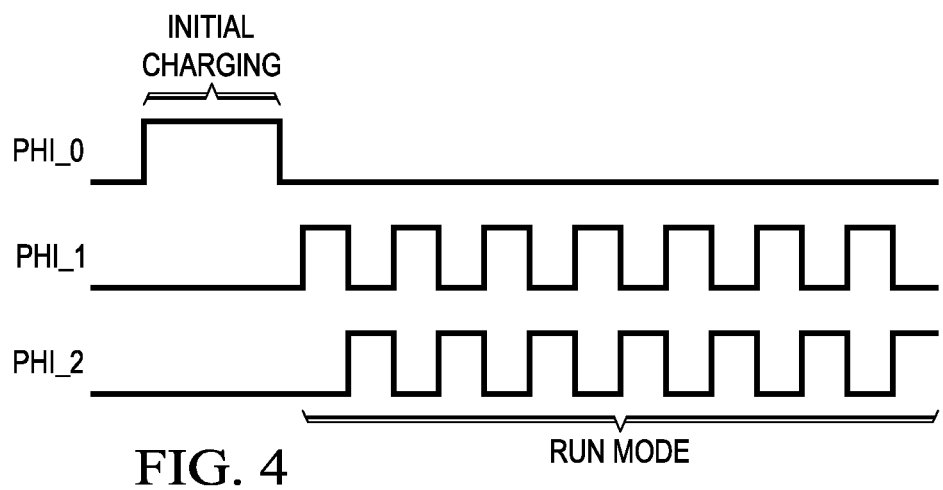
FIG. 4 illustrates in a simplified timing diagram the operation of control signals used for the bootstrap circuit of FIG. 3.

FIG. 4 illustrates a timing diagram for the control signals PHI_0, PHI_1, and PHI_2 for use in describing the operations of the circuit in FIG. 3. During an initial time period, labeled "Initial charging," the control signal PHI_0 closes switches 53 and 59. In the "Initial charging" period, the bootstrap capacitor Cb is coupled between Vin and a low voltage VSS. VSS may be set to a middle level voltage between VDD and VEE, and may be calibrated depending on the voltage levels of Vin and the level of Vout desired. During this initial charging period the bootstrap capacitor Cb is charged to the voltage (Vin-VSS). After the "Initial charging" period ends, the circuit is operated in a "Run" mode. In the "Run" mode, the two control signals PHI_1 and PHI_2 are operated as non-overlapping periodic control signals of approximately equal duration, however the two signals PHI_1 and PHI_2 are not high at the same point in time. Put another way, these periodic control signals can have similar duty cycles but do not overlap. When PHI_2 is high, in the "off" state for the switch implemented by transistor M1 in FIG. 3, the bottom plate of the capacitor Cb is coupled to VEE, the lowest supply voltage. The switch transistor M1 is OFF in this phase, as the bottom plate of capacitor Cb is at a lower voltage than the charged voltage.

In the "Run" mode, when the control signal PHI_1 is high, the voltage VDD is coupled to the bottom plate of capacitor Cb. In this mode the switch implemented by transistor M1 is closed, so that the input voltage Vin is coupled to the output Vout by the current conduction path of the transistor. To close the switch implemented by MOS transistor M1, the gate terminal is at the voltage VDD+(Vin−VSS). The source terminal is now at the voltage (Vin), and so the gate-to-source voltage Vgs is now at the potential VDD+Vin−Vin−Vss, or simply VDD-VSS. The transistor M1 is now on. Importantly, the gate-to-source voltage Vgs for transistor M1, which the on-resistance Rdson is proportional to, is at VDD-VSS and is independent of the variable voltage Vin. When the on-resistance is the same for each sampling cycle, the ADC circuit has improved linearity because the on-resistance Rdson of transistor M1 is determined by a constant voltage that does not depend on Vin.

Figure 5:
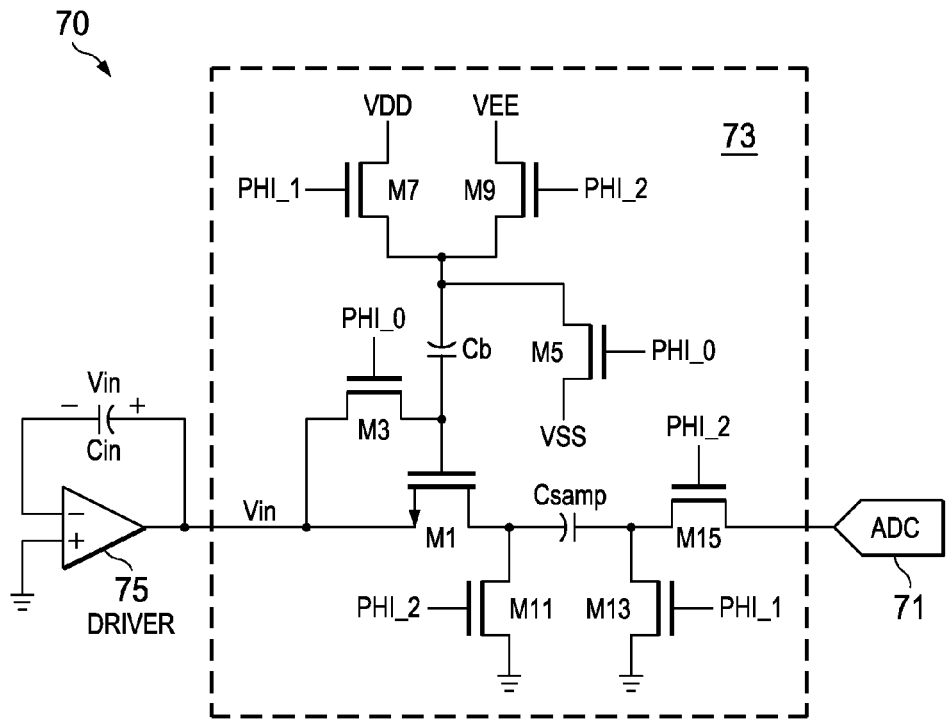
FIG. 5 in a simplified circuit diagram an example illustrative implementation for a novel bootstrap circuit incorporating features of the present application into an analog to digital converter arrangement.

FIG. 5 depicts an example implementation of an illustrative arrangement incorporating features of the present application 70 including a bootstrap circuit. In FIG. 5, a bootstrap circuit 73 is shown in an ADC converter 70. A driver stage is formed by capacitor Cin with the analog voltage Vin stored across it, and operational amplifier 75. The amplifier 75 drives the remaining portions of the circuit. Due to the operation of the capacitor and operational amplifier circuit, driver 75 has a voltage Vin at its output as described above.

In the illustrative arrangement of FIG. 5, the transistor M1 is configured as an input sampling switch for the sampling capacitor Csamp. The three phase control signal scheme described above is used to control the bootstrap circuitry 73 and performs the sampling of the voltage Vin onto the capacitor Csamp and into the ADC 71.

During the initial charging period, the control signal PHI_0 is high and the capacitor Cb is charged to the voltage Vin-VSS by operation of the transistors M3 and M5, as described above with respect to FIGS. 3 and 4. During the run mode, the periodic control signals PHL_1 and PHI_2 repeatedly sample the output of the driver 75 by turning the transistor M1 on, and then off. In this example illustrative arrangement incorporating features of the present application, the switches are implemented by N-type MOS transistors. Accordingly when PHL_1 is active, the bottom plate of capacitor Cb is coupled to the positive supply voltage VDD by transistor M7. The bootstrap capacitor Cb is already charged to the voltage Vin, as described above, and now boosts the gate of transistor M1 to a voltage VDD+Vin. The source voltage of transistor M1 is at Vin, as described above, and so the gate to source voltage Vgs for transistor M1 is now simply VDD. Transistor M13 is also active due to the high voltage level of signal PHI_1, and the capacitor Csamp thus receives the voltage Vin from driver 75 through the current conduction path of transistor M1.

When control signal PHI_2 is active, the gate of sampling transistor M1 is coupled by transistor M9 to the lowest voltage in the system, VEE, by capacitor Cb, and is turned off. Also, the transistors M11 and M15 in FIG. 5 are active due to the high voltage level on control signal PHI_2 and the sampling capacitor Csamp transfers the stored voltage into the analog to digital converter ADC 71.

In this illustrative example implementation, N-type MOS transistors can be used for transistors M3, M5, M7, M9 to form the switches for the bootstrap circuit for turning on transistor M1, and also for transistors M11, M13, M15 for operating the sampling circuit for capacitor Csamp. However the embodiments are not to be limited to this illustrative example implementation, and additional transistor types can also be used such as P-type MOS transistors, bipolar and bi-CMOS transistors, enhancement and depletion mode transistors, and the like. Use of these alternative transistor types form additional alternative arrangements that are also contemplated as additional aspects of the present application, and which fall within the scope of the appended claims.

Figure 6:
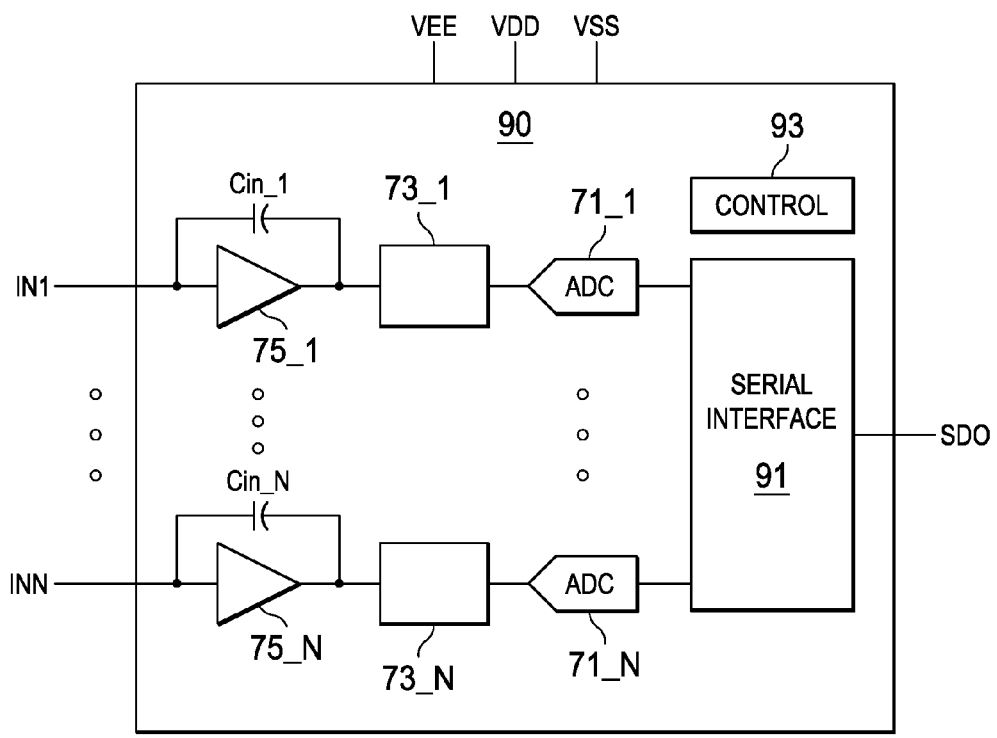
FIG. 6 illustrates in a simplified block diagram a novel analog to digital converter integrated circuit incorporating the bootstrap circuit features of the present application.

FIG. 6 illustrates in a block diagram an analog to digital converter integrated circuit (ADC IC) 90, which may also be described as an analog front end (AFE), incorporating an illustrative arrangement bootstrap circuit that achieves the advantages accrued by use of the features of the present application discovered by the inventors. In FIG. 6, a plurality of analog inputs IN1-INN are shown coupled to input pins of the ADC IC 90. For each of a plurality of channels 1-N, an integrator is formed by the amplifiers 75_1-75_N, and the respective integrator capacitors Cin_1-Cin_N. Alternatively, some of the channels can be shared and using multiplexers, selectively coupled to the input pins to form additional alternative embodiments that are also contemplated herein. A bootstrap circuit 73 including the switches and sampling capacitors such as, for example, as are described above in FIG. 5, are provided for each of the 1-N channels and are labeled 73_1-73_N. An analog to digital converter 71_1-71_N is coupled to each of the sampling capacitors in blocks 73_1-73_N. In the ADC IC 90 the output digitized data is input to a serial interface block 91 and output as serial data SDO to the system.

Control circuit 93 provides various control signals and can provide the control signals PHI_0, PHI_1 and PHI_2, as described above, and other control signals. Various modifications to the illustrative example architecture of ADC IC 90 can be used to form additional arrangements that are contemplated as additional aspects of this application and which are encompassed by the appended claims.

Figure 7:
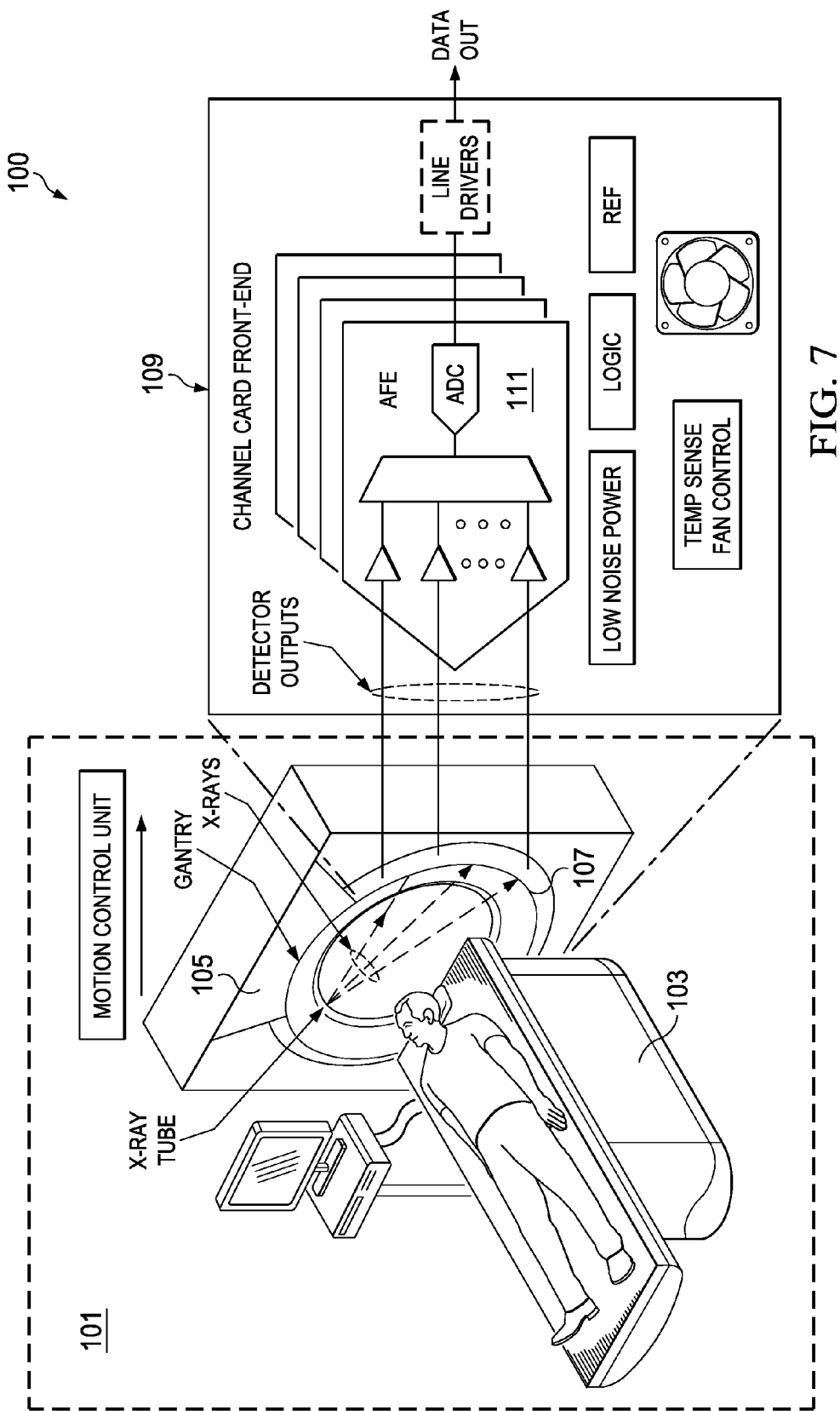
FIG. 7 illustrates in a simplified block diagram an example application for a CT scanner system incorporating circuits including the novel bootstrap circuits of the present application.

FIG. 7 depicts in a simplified block diagram an illustrative CT scan arrangement 100 incorporating the bootstrap circuits for the sampling switch in FIG. 3 and/or the ADC IC in FIG. 6, for example. The CT scanner may be described as "related end equipment" for an analog to digital converter; however, the features of the present application are not so limited and may be incorporated in any system with a bootstrapped circuit for a sampling switch as described above. In FIG. 7, a CT scan system 100 is depicted as including a CT scanning module 101 using a patient table 103 and a movable gantry 105. The gantry moves the patient into an X-ray tube 107 which includes a plurality of X-ray emitters and corresponding X-ray sensitive detectors such as photo-detectors. Analog output signals labeled "Detector Outputs" corresponding to the intensity of the X-ray radiation sensed by the photo-detectors are shown coupled to a Channel Card Front End 109. The Channel Card Front End 109 includes a plurality of the ADC ICs 111, these can be ADC IC arrangements such as 90 in FIG. 6, or other integrated circuit ADCs which each incorporate the bootstrap circuit for the sampling switch of the arrangements having features of the present application such as are illustrated in FIG. 3, FIG. 5 as described above. Digital output data Data Out is then output by the Channel Card Front End 109 and is thus available for digital signal processing for various additional processes. For example the digital data can be used to form CT scan images for display and storage. The Channel Card Front End can include as many of the ADC IC devices as are needed for a particular application, depending on the number of analog output signals there are from the photo-detectors.

The CT scan system of FIG. 7 is but one non-limiting example application for the arrangements and features of the present application. However the arrangements described including the bootstrap circuit for the sampling switch discovered by the inventors may be used in any switched capacitor application. In particular the bootstrap circuit of the features of the present application provides advantages for any ADC that uses a switched capacitor to sample an input signal that is oversampled. Advantages attained by use of the various arrangements of the present application include that the driver amplifier or other driver of a sampling switch does not have to repeatedly charge the bootstrap capacitor; instead the driver charges the bootstrap capacitor with the input signal only during the initial period where the input voltage Vin is stored on the bootstrap capacitor. The driver is then relieved from driving the bootstrap capacitor and the gate capacitor of the sampling switch. The driver is also coupled to the top plate of the bootstrap capacitor, which has a lower parasitic capacitance value than the bottom plate of the bootstrap capacitor which the driver circuit in the prior known solutions has to drive.

Because the features of the present application discovered by the inventors also provide a gate voltage on the sampling switch of a supply voltage level such as VDD that is independent of the analog voltage Vin, the ADC circuit that results using the arrangements of the present application is highly linear and has excellent performance. The power savings attained by use of the arrangements that incorporate various features of the present application is significant.

In an example implementation, the driver circuit for a resettable delta sigma ADC was configured using the bootstrap circuit of an illustrative arrangement of the present application such as shown in FIG. 3 above. For a driver requiring a bandwidth of about 40 MHz, with a switching load of 5 picoFarads or pF, the effective bottom place parasitic capacitance was observed to be about 500 femtoFarads or fF. By using the novel bootstrap circuit of the present application and thereby advantageously relieving the driver circuit from having to repeatedly charge the bottom plate capacitance, the direct power reduction of about 10% is seen simply by considering the small signal constraints.

Figure 2:
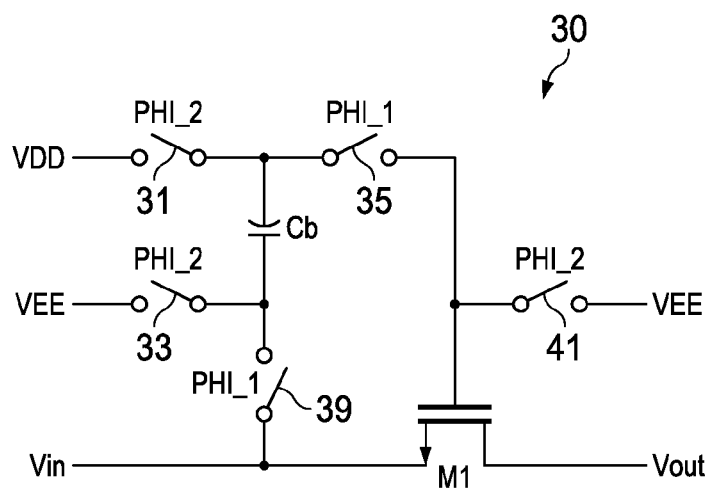
FIG. 2 illustrates in a simplified circuit diagram a prior art bootstrap circuit for a switch used in the circuit depicted in FIG. 1A.

The driver amplifier in the arrangements discovered by the inventors of the present application is advantageously relieved of the need to drive the bottom plate of the bootstrap capacitor and the gate of the sampling transistor each time the on portion of the switched capacitor circuit is active. The gate voltage in the on portion of the conversion cycle is provided by VDD and the charged bootstrap capacitor, not by the driver amplifier. In sharp contrast to the advantageous arrangements incorporating features of the present application, in the prior known solutions such as in FIG. 2 above, the load step seen by the driver circuit due to repeatedly driving the bootstrap circuit and the gate capacitance of the sampling transistor increases the power consumption and increases the possible non-linearity problems of the circuit still further, because the driver has to provide the slew current to turn on the sampling transistor many times during each conversion cycle. In a surprising discovery by the inventors of the present application, in the arrangements a suitable switching scheme is used to ensure that the sampling capacitor is changed to a coarse value of the input voltage, Vin, unexpectedly alleviating the need for the driver circuit to provide significant slew current. In contrast, in a prior known solution having the same driver circuit, the slew current required to drive the bottom plate parasitic capacitance of the boost capacitor is quite significant. Use of the novel bootstrap arrangements discovered by the inventors of the present application thus enables significant reduction in power dissipation.

Use of the bootstrap arrangements incorporating features of the present application therefore further advantageously reduces the driver power by approximately another additional 10%. Thus there is a net power savings of about 20% attained by use of the novel bootstrap circuits described above and incorporating features of the present application for the sampling transistor for a switched capacitor input stage, when compared to the bootstrap circuits of the prior known solutions.

Although the example illustrative arrangements have been described in detail, it should be understood that various changes, substitutions and alterations can be made herein without departing from the spirit and scope of the application as defined by the appended claims.

Moreover, the scope of the present application is not intended to be limited to the particular illustrative examples of the process, machine, manufacture, and composition of matter, means, methods and steps incorporating the features of the present application that are described in the specification. As one of ordinary skill in the art will readily appreciate from the disclosure, processes, machines, manufacture, compositions of matter, means, methods or steps, presently existing or later to be developed, that perform substantially the same function or achieve substantially the same result as the corresponding example arrangements described herein may be utilized according to the illustrative arrangements and alternative arrangements. Accordingly, the appended claims are intended to include within their scope such processes, machines, manufacture, compositions of matter, means, methods, or steps.

What is claimed is:

1. A bootstrap circuit for a sampling transistor for a switched capacitor, comprising:
    a MOS transistor having a source terminal coupled to an input for receiving an input voltage;
    an output at a drain terminal of the MOS transistor coupled to one plate of a sampling capacitor;
    a first switch coupling the input voltage to a gate terminal of the MOS transistor responsive to an initial phase control signal;
    a bootstrap capacitor having a top plate coupled to the gate terminal of the MOS transistor and coupled to the first switch;
    a second switch coupling a bottom plate of the bootstrap capacitor to a first low voltage supply responsive to the initial phase control signal;
    a third switch coupling the bottom plate of the bootstrap capacitor to a positive voltage supply greater than the first low voltage supply responsive to a first phase periodic control signal; and
    a fourth switch coupling the bottom plate of the bootstrap capacitor to a second low voltage supply lower than the first low voltage supply, responsive to a second phase periodic control signal.

2. The bootstrap circuit of claim 1, wherein the first switch and the second switch are closed during an initial phase responsive to the initial phase control signal, coupling the top plate of the bootstrap capacitor to the input voltage and charging the bootstrap capacitor to the input voltage.

3. The bootstrap circuit of claim 2, wherein the third switch is closed during each high portion of the first phase periodic control signal, boosting the gate voltage of the MOS transistor to a voltage that is a sum of the input voltage stored on the bootstrap capacitor and the positive supply voltage.

4. The bootstrap circuit of claim 3, wherein the fourth switch is closed during each high portion of the second phase periodic control signal, coupling the gate of the MOS transistor to the second low voltage plus the input voltage stored on the bootstrap capacitor.

5. The bootstrap circuit of claim 3, wherein the input voltage is coupled to the sampling capacitor during each high portion of the first phase periodic control signal by a current conduction path of the MOS transistor, which is turned on by the boosted gate voltage.

6. The bootstrap circuit of claim 1, wherein the MOS transistor is an N-type MOS transistor.

7. The bootstrap circuit of claim 1, wherein each of the first, second, third and fourth switches comprise a MOS transistor.

8. The bootstrap circuit of claim 7, wherein the first, second, third and fourth switches each comprise an N-type MOS transistor.

9. The bootstrap circuit of claim 1, wherein the initial phase control signal is high only for an initial portion of a sampling cycle, and the first phase periodic control signal and the second phase periodic control signal are repeating periodic signals that continue for a remaining portion of the sampling cycle, the first and the second periodic control signals having similar duty cycles that are non-overlapping.

10. An analog to digital converter integrated circuit, comprising:
a plurality of inputs each configured to receive an analog input signal;
a plurality of resettable delta sigma analog to digital converter stages, each comprising:
a plurality of driver circuits, each coupled to a respective one of the plurality of inputs, each comprising an amplifier and an integrator capacitor and outputting a sampled input voltage;
a plurality of switched capacitor input stages, each coupled to receive at least one of the sampled input voltages at an input, each of the switched capacitor input stages further comprising:
the input receiving the sampled input voltages and coupled to a source terminal of a MOS transistor;
an output at a drain terminal of the MOS transistor coupled to one plate of a sampling capacitor;
a first switch coupling the input to a gate terminal of the MOS transistor, responsive to an initial phase control signal;
a bootstrap capacitor having a top plate coupled to a gate terminal of the MOS transistor and to the first switch;
a second switch coupling a bottom plate of the bootstrap capacitor to a first low voltage supply responsive to the initial phase control signal;
a third switch coupling the bottom plate of the bootstrap capacitor to a positive voltage supply greater than the first low voltage supply responsive to a first phase periodic control signal; and
a fourth switch coupling the bottom plate of the bootstrap capacitor to a second low voltage supply lower than the first low voltage supply, responsive to a second phase periodic control signal.

11. The analog to digital converter circuit of claim 10, and further comprising: control circuitry coupled to provide the initial phase control signal at an initial portion of a sampling operation, and further coupled in a run portion of the sampling operation to subsequently provide the first phase periodic control signal and the second phase periodic control signal as repeating periodic signals that are non-overlapping.

12. The analog to digital converter circuit of claim 10, and further comprising a plurality of analog to digital converter stages coupled to respective ones of the sampling capacitors and configured to output digital data corresponding to the analog input signals.

13. The analog to digital converter circuit of claim 10, wherein the MOS transistors are N-type MOS transistors.

14. The analog to digital converter circuits of claim 10, wherein during a high portion of the first phase periodic control signal, the voltage input at the source of the MOS transistors is coupled to the drain of the MOS transistors and to the sampling capacitor, due to the gate to source voltage of the MOS transistors which is boosted by the bootstrap capacitor to the positive supply voltage.

15. A system for imaging, comprising:
an apparatus for creating images comprising a plurality of radiation emitters spaced from and directed towards a plurality of photo-detectors sensitive to the emitted radiation, the plurality of photo-detectors outputting analog output signals corresponding to an intensity of the radiation received at the photo-detectors;
at least one analog-to-digital converter integrated circuit having a plurality of inputs coupled to receive analog output signals from the plurality of photo-detectors, and further comprising:
a plurality of analog to digital converter stages including an analog-to-digital converter stage configured to output digital data corresponding to the analog output signals, each of the analog to digital converter stages comprising:
a plurality of driver circuits, each coupled to a respective one of the plurality of inputs, each comprising an amplifier and a capacitor coupled to sample an analog signal and each outputting a corresponding input voltage;
a plurality of switched capacitor input stages, each coupled to the output of at least one of the driver circuits, each of the switched capacitor input stages further comprising:
a MOS sampling transistor having a current conduction path coupled between the input voltage and an output, and having a gate terminal;
one plate of a sampling capacitor coupled to the output of the MOS sampling transistor;
a first switch coupling the input voltage to the gate terminal of the MOS sampling transistor, responsive to an initial phase control signal;
a bootstrap capacitor having a top plate coupled to the gate terminal of the MOS sampling transistor and to the first switch;
a second switch coupling a bottom plate of the bootstrap capacitor to a first low voltage supply responsive to the initial phase control signal;
a third switch coupling the bottom plate of the bootstrap capacitor to a positive voltage supply greater than the first low voltage supply, responsive to a first phase periodic control signal; and
a fourth switch coupling the bottom plate of the bootstrap capacitor to a second low voltage supply lower than the first low voltage supply, responsive to a second phase periodic control signal.

16. The system for imaging of claim 15, wherein the MOS sampling transistors in each of the switched capacitor input stages further comprise an N-type MOS transistor.

17. The system for imaging of claim 15, wherein the first, second, third and fourth switches of each of the switched capacitor input stages further comprise MOS transistors.

18. The system for imaging of claim 15, and further comprising:
   a control circuit within the analog to digital converter integrated circuit, the control circuit outputting the initial phase control signal at an initial portion of an analog signal conversion cycle, and subsequently outputting for a remaining portion of an analog signal conversion cycle the first periodic control signal and the second periodic control signal as repeating periodic signals are non-overlapping.

19. The system for imaging of claim 15, wherein the system is a computed tomography X-ray scanning system.

20. The system for imaging of claim 15, wherein the system is an X-ray baggage scanning system.

* * * * *